United States Patent [19]

Au

[11] 4,389,411
[45] Jun. 21, 1983

[54] CYANO-(2,4-DICHLOROPHENYL)METHYL ETHYL ESTER OF CARBONIC ACID USEFUL AS A NEMATOCIDE

[75] Inventor: Andrew T. Au, Needham, Mass.
[73] Assignee: The Dow Chemical Company, Midland, Mich.
[21] Appl. No.: 354,479
[22] Filed: Mar. 3, 1982
[51] Int. Cl.³ .................... A01N 47/06; C07C 121/75
[52] U.S. Cl. .................................... 424/301; 260/463
[58] Field of Search .......................... 260/463; 71/105; 424/301

[56] References Cited

U.S. PATENT DOCUMENTS

| | | | |
|---|---|---|---|
| 3,124,608 | 3/1964 | Schisla et al. | 260/463 |
| 3,306,880 | 2/1967 | Lee et al. | 260/77.5 |
| 3,377,155 | 4/1968 | Weil et al. | 71/105 |
| 3,594,400 | 7/1971 | Boogaart et al. | 260/463 |
| 3,723,625 | 3/1973 | Boogaart et al. | 424/301 |
| 3,835,176 | 9/1974 | Matsuo et al. | 260/465 D |

FOREIGN PATENT DOCUMENTS 1122658  8/1965  United Kingdom .

OTHER PUBLICATIONS

Hibernia–Chemie G.m.b.H., Chemical Abstracts, vol. 65, 5374g (1966).
Uff et al., "Formation of Cyanohydrin Carbonates of Aromatic Aldehydes and Aryl Heteroaryl Ketones, Synthetic Communications," 8 (3), 163–167, (1978).

Primary Examiner—Donald G. Daus
Assistant Examiner—Diana G. Rivers
Attorney, Agent, or Firm—Norman L. Sims; Douglas N. Deline

[57] ABSTRACT

Disclosed as a novel compound is cyano-(2,4-dichlorophenyl)methyl ethyl ester of carbonic acid. This compound has utility as a nematocide.

4 Claims, No Drawings

CYANO-(2,4-DICHLOROPHENYL)METHYL ETHYL ESTER OF CARBONIC ACID USEFUL AS A NEMATOCIDE

BACKGROUND OF THE INVENTION

Various alpha-cyano carbonates are taught in the literature. Cyanophenylmethyl ethyl ester of carbonic acid and the method of preparing such is taught by Uff et al. in "Formation of Cyanohydrin Carbonates of Aromatic Aldehydes and Aryl Heteroaryl Ketones", *Synthetic Communications*, 8 (3), 163-167 (1978).

SUMMARY OF THE INVENTION

The present invention is directed to the compound cyano-(2,4-dichlorophenyl)methyl ethyl ester of carbonic acid. This compound has been found to be an active root knot nematode control agent. This compound is represented by the formula

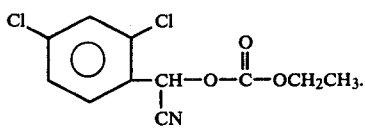

The compound of the invention is an oily liquid which is substantially insoluble in water, slightly soluble in nonpolar hydrocarbons and substantially soluble in polar organic solvents.

The cyano-(2,4-dichlorophenyl)methyl ethyl ester of carbonic acid may be prepared by contacting a solution of 2,4-dichlorobenzaldehyde and ethylchloroformate in a nonreactive water-immiscible organic solvent, such as methylene chloride, with an aqueous solution of a metal cyanide, preferably an alkali or alkaline earth metal cyanide, such as sodium cyanide, and if desired, a catalyst such as a phase transfer "onium" salt such as tetra-n-butylammonium chloride or benzyltrimethylammonium chloride, and stirring the mixture for about 1 hour to several days, preferably about 3 to 6 hours. The product can then be recovered by washing, drying and concentrating the organic layer.

Between about 0.1 and 40.0 equivalents of ethyl chloroformate for each equivalent of 2,4-dichlorobenzaldehyde may be used, and between about 1.0 and 1.2 is preferred. Between about 1.0 and 20.0 equivalents of the metal cyanide per equivalent of the 2,4-dichlorobenzaldehyde may be used, and between about 1.5 and 2.0 equivalents is preferred. The phase transfer catalyst may be present between about 0 and 10.0 equivalents per equivalent of 2,4-dichlorobenzaldehyde, and between about 0.01 and 0.1 equivalent is preferred. The reaction may be run with or without the catalyst. The reaction may be run at a temperature between about $-30°$ C. and $60°$ C., and between about $-10°$ C. and $25°$ C. is preferred.

DESCRIPTION OF SOME PREFERRED EMBODIMENTS

The following example illustrates the present invention and the manner by which it can be produced, but, as such, should not be construed as a limitation upon the overall scope of the invention.

EXAMPLE 1

To a stirred solution of 2.0 g of sodium cyanide in 10 ml of water and a catalytic amount of tetra-n-butylammonium chloride at 0° C. was added dropwise 30 ml of methylene chloride containing 3.5 g of 2,4-dichlorobenzaldehyde and 2.2 g of ethylchloroformate. The mixture was stirred overnight while being warmed to room temperature. Gas chromatography showed that the starting materials had disappeared. The organic layer was washed with water, followed by a saturated bicarbonate solution, then dried over magnesium sulfate and concentrated to 5.1 g of a yellow oil giving a yield of 92.7 percent. Thin-layer chromatography, nuclear magnetic resonance spectroscopy and infrared spectroscopy all showed the product to be cyano-(2,4-dichlorophenyl)methyl ethyl ester of carbonic acid.

The compound of the present invention is useful as a pesticide and has particular utility as a nematocide. The compound can be employed as a pesticide by distributing the compound, in a pesticidally effective quantity and usually in the form of a composition containing adjuvants (such as an inert horticultural carrier) to aid in dispersing the same, so as to contact directly the organism to be controlled or, alternatively, so as to contact the growth medium or habitat of the organisms whereby eventual contact with said organisms will be established. In the control of nematodes, good results are obtained by distributing the active compound in soil in amounts of from about 1 to 2500 parts or more per million parts by weight of soil.

The concentration of active compound in liquid compositions generally is from about 0.0001 to 50 percent by weight. Concentrations up to 95 percent by weight are oftentimes conveniently employed, particularly in concentrate compositions. In dusts, the concentrations of the active compound can be from about 0.1 to 95 percent by weight. In compositions to be employed as concentrates, the active compounds can be present in a concentration of from 5 to 98 percent by weight. For use as a spray, it is often convenient to prepare the compounds as wettable powders.

For such nematocidal applications, the active compound hereof can be employed in unmodified form or in the form of a liquid or finely divided solid composition. Thus, the compound can be dispersed in a finely divided solid and employed as dusts. The compound and such solid dispersions can also be dispersed in water with or without the aid of a surface active agent and the resulting aqueous suspensions be employed as drenches or sprays for application to soil, weeds or otherwise. In other procedures, the compound is employed as an active constituent in solvent solutions, oil-in-water or water-in-oil emulsions or aqueous dispersions. The augmented compositions are adapted to be formulated as concentrates and subsequently diluted with additional liquid or solid adjuvants to produce the ultimate treating compositions.

In a representative operation, cyano-(2,4-dichlorophenyl)methyl ethyl ester of carbonic acid, at a concentration of 2400 parts per million by weight of solution, was sprayed on plants planted in soil infected with root knot nematodes and was found to give 90 percent control of the nematodes.

What is claimed is:
1. Cyano-(2,4-dichlorophenyl)methyl ethyl ester of carbonic acid.
2. A method for controlling nematodes which comprises subjecting the nematodes to the compound of claim 1.

3. A nematocidal composition comprising an inert horticultural carrier and as a nematocide, the compound of claim 1, the concentration of said nematocide being from 0.0001 to 50 percent by total weight of the composition.

4. A method for protecting plants from attack from nematodes which comprises treating the plants to be protected with an effective dosage of the compound of claim 1.

* * * * *